(12) United States Patent
Smith

(10) Patent No.: US 9,707,372 B2
(45) Date of Patent: Jul. 18, 2017

(54) SYSTEM AND METHOD FOR A BIORESONANCE CHAMBER

(75) Inventor: Rosalind Y. Smith, Rainier, WA (US)

(73) Assignee: Rosalind Y. Smith, Nokomis, FL (US)

( * ) Notice: Subject to any disclaimer, the term of this patent is extended or adjusted under 35 U.S.C. 154(b) by 561 days.

(21) Appl. No.: 13/194,827

(22) Filed: Jul. 29, 2011

(65) Prior Publication Data

US 2013/0030241 A1    Jan. 31, 2013

(51) Int. Cl.
*A61M 21/00* (2006.01)
*A61M 21/02* (2006.01)

(52) U.S. Cl.
CPC ........ *A61M 21/0094* (2013.01); *A61M 21/00* (2013.01); *A61M 21/02* (2013.01); *A61M 2021/0027* (2013.01); *A61M 2021/0038* (2013.01); *A61M 2021/0055* (2013.01); *A61M 2021/0066* (2013.01); *A61M 2205/3584* (2013.01); *A61M 2205/502* (2013.01); *A61M 2230/005* (2013.01); *A61M 2230/04* (2013.01); *A61M 2230/10* (2013.01); *A61M 2230/65* (2013.01)

(58) Field of Classification Search
CPC ............................................ A61M 2021/0038
USPC ................. 600/26–28, 21, 22; 128/897–899; 4/541.1
See application file for complete search history.

(56) References Cited

U.S. PATENT DOCUMENTS

| | | | | |
|---|---|---|---|---|
| 3,585,991 A * | 6/1971 | Balamuth | ...... | 601/157 |
| 4,738,266 A * | 4/1988 | Thatcher | ...... | 600/473 |
| 5,036,858 A * | 8/1991 | Carter et al. | ...... | 600/545 |
| 5,099,587 A * | 3/1992 | Jarosch | ...... | 34/202 |
| 5,267,942 A * | 12/1993 | Saperston | ...... | 600/28 |
| 5,903,934 A * | 5/1999 | Sears, III | ...... | 4/538 |
| 6,409,654 B1 * | 6/2002 | McClain | ...... | 600/22 |
| 6,523,191 B2 * | 2/2003 | Lahay et al. | ...... | 4/541.1 |
| 7,578,783 B2 * | 8/2009 | Klein | ...... | 600/27 |
| 8,424,127 B2 * | 4/2013 | An | ...... | 4/541.1 |
| 2002/0011482 A1 * | 1/2002 | Gordon | ...... | 219/480 |
| 2006/0183980 A1 * | 8/2006 | Yang | ...... | 600/301 |
| 2008/0063363 A1 * | 3/2008 | Kientz et al. | ...... | 386/95 |
| 2008/0214949 A1 * | 9/2008 | Stivoric et al. | ...... | 600/549 |
| 2009/0241254 A1 * | 10/2009 | Glasford et al. | ...... | 4/541.1 |
| 2010/0174586 A1 * | 7/2010 | Berg et al. | ...... | 705/10 |
| 2010/0179371 A1 * | 7/2010 | Pletnev et al. | ...... | 600/9 |
| 2010/0222638 A1 * | 9/2010 | Chilton, III | ...... | 600/22 |
| 2011/0042471 A1 * | 2/2011 | Futaeda et al. | ...... | 236/51 |
| 2011/0087096 A1 * | 4/2011 | Behar | ...... | 600/438 |
| 2012/0149973 A1 * | 6/2012 | Holloway | ...... | 600/28 |
| 2012/0157757 A1 * | 6/2012 | Ten Eyck et al. | ...... | 600/22 |
| 2013/0236865 A1 * | 9/2013 | Hamui | ...... | 434/236 |

* cited by examiner

*Primary Examiner* — Charles A Marmor, II
*Assistant Examiner* — Shannon McBride
(74) *Attorney, Agent, or Firm* — Perkins Coie LLP

(57) ABSTRACT

A technique for influencing the human brain can be applied to treat PTSD through stimulating the brain with a beat in, for example, the theta (θ) frequency to influence the brain to relax. Alternatively, the human brain can be stimulated with a beat in the alpha (α) frequency to stimulate active thinking. Over a series of treatments the brain of an individual suffering from PTSD can be influenced to operate at a normal frequency. Advantageously, as the frequency is adjusted, the symptoms of PTSD recur less often until the individual ceases to experience the symptoms or has at least experienced a decreased recurrence of the symptoms.

22 Claims, 5 Drawing Sheets

SYSTEM AND METHOD FOR A BIORESONANCE CHAMBER

BACKGROUND

Posttraumatic stress disorder (PTSD) is an anxiety disorder resulting from exposure to shocking and/or distressing events. Many veterans experience PTSD because of their wartime experiences. For example, PTSD can result in persistent flashbacks, nightmares, difficulty sleeping, and significant impairment of social and occupational function.

PTSD is understood to result in neuroendocrinological changes as well, as brain morphology. As a result, some patients are known to have atypical biochemical levels associated with the sympathetic nervous system, or the system that controls the "fight or flight" response. Fear is thought to be closely associated with these neurobiological conditions.

Various attempts have been made to treat PTSD including psychotherapy, medication, and combinations of therapies. However, while medications have shown benefit in reducing PTSD symptoms, there is no clear drug treatment for PTSD. This may be because such treatment is symptom-oriented and does not necessarily cause the patient to recover from the disorder.

Alternative approaches to solving the problems presented by PTSD could desirably treat the neurobiological conditions established by the traumatic events rather than merely reducing the symptoms suffered by patients experiencing PTSD. For example, psychological and neuropsychological studies suggest a correlation with treating areas of the human brain, such as the hippocampus and amygdale, and improvement for veterans suffering with PTSD.

The foregoing examples of the related art and limitations related therewith are intended to be illustrative and not exclusive. Other limitations of the related art will become apparent upon a reading of the specification and a study of the drawings.

SUMMARY

The following examples and aspects thereof are described and illustrated in conjunction with systems, tools, and methods that are meant to be exemplary and illustrative, not limiting in scope. In various examples, one or more of the above-described problems have been reduced or eliminated, while other examples are directed to improvements.

A technique for influencing the human brain can be applied to treat neurobiological conditions through influencing the brain to operate at a desired, therapeutic frequency by producing specific sound beats, which are converted by the inner ear into electrical signals received by the hippocampus. For example, the human brain can be stimulated with a beat in the theta (θ) frequency range to influence the brain to relax and enter into a therapeutic state. Alternatively, the human brain can be stimulated with a beat in the alpha (α) frequency range to stimulate active thinking. Over a series of treatments the brain of an individual suffering from PTSD, or other neurobiological conditions, can be influenced to operate at a normal frequency. Advantageously, as the frequency is adjusted, the symptoms of PTSD recur less often until the individual ceases to experience the symptoms or has at least experienced a decreased recurrence of the symptoms.

A system for influencing a human brain to operate at a frequency includes a fluid filled chamber having various audio reproduction devices. The audio reproduction devices are coupled to a processing device producing audio signals prepared to influence the human brain to operate at a frequency conducive to function in a particular therapeutic state. The audio reproduction devices can produce waves in both audible and inaudible frequencies. In response to the stimulation, cells within the human brain can respond to the audio frequencies by influencing cellular water action potential. In one implementation, multiple frequencies can be combined into a monaural beat, a single united resonance frequency to induce the therapeutic state. Monitoring devices can be distributed inside and/or outside the chamber to record the brainwaves emanating from the human brain.

A method for influencing a human brain of an individual to operate at a frequency includes stimulating the human brain with audio waves while the individual is floating in a fluid medium. While stimulated, the individual can be monitored for adherence to the frequency using one or more sensors to identify the frequency of operation of the individual's brain waves. In one implementation the audio waves can be projected through the fluid medium in more than one frequency where the difference between the frequencies produce a monaural beat stimulating the human brain at the desired frequency. Additionally, the audio waves can be interspersed with music to provide an engaging experience.

In one embodiment, monaural beats are produced based on the acoustical design of a chamber shaped to optimize delivery of frequencies to an individual within the chamber. In a further embodiment, the shape of the chamber is designed based on the acoustical characteristics of a musical instrument, such as the cello.

DETAILED DESCRIPTION

In the following description, several specific details are presented to provide a thorough understanding. One skilled in the relevant art will recognize, however, that the concepts and techniques disclosed herein can be practiced without one or more of the specific details, or in combination with other components. In other instances, well-known implementations or operations are not shown or described in detail to avoid obscuring aspects of various examples disclosed herein.

Figure 1:
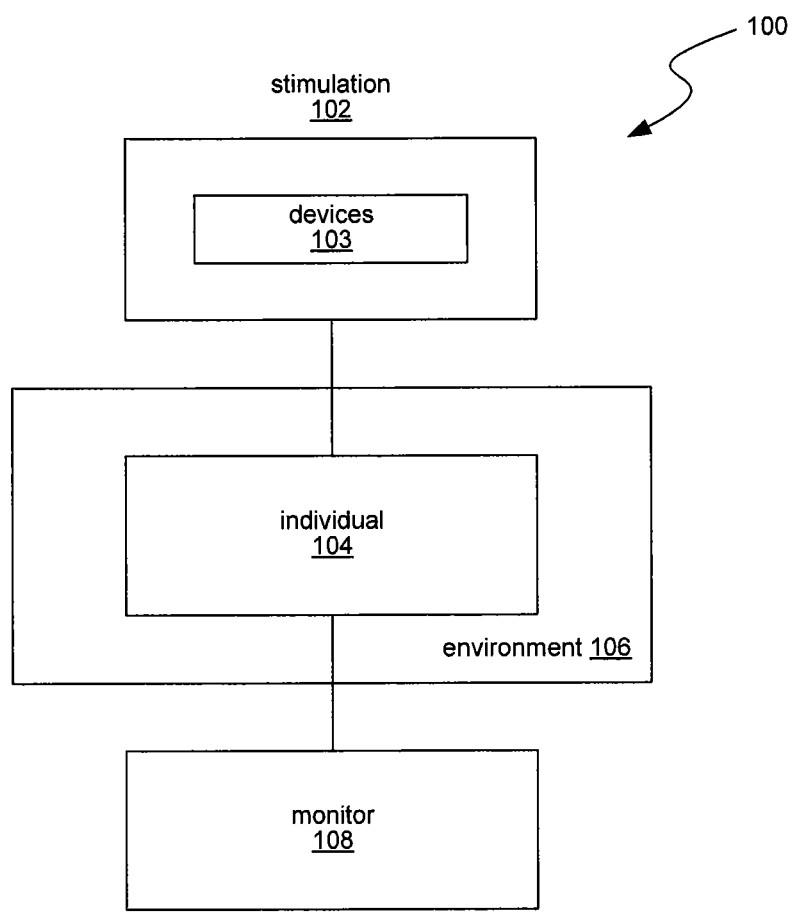
FIG. 1 depicts an example of a system for influencing a human brain to operate at a frequency.

FIG. 1 depicts an example of a system 100 for influencing a human brain to operate at a frequency. FIG. 1 includes stimulation module 102, individual 104, environment 106, and monitor 108.

In the example of FIG. 1, the stimulation module 102 can include devices 103 for producing audible, vibratory, magnetic or other known or convenient signals. For example, the stimulation module 102 can include devices 103 such as speakers, one or more ultrasonic transducers, or other known or convenient devices for stimulating an individual 104 while the individual 104 is within environment 106. The stimulation provided by devices 103 can be administered at a predetermined, desired frequency, or an individual 104 can adjust the frequency to a desired level corresponding to the type of therapy that the individual 104 desires to undertake. The devices 103 can produce therapeutic effects by inducing cellular regeneration and brainwave entrainment.

In the example of FIG. 1, environment 106 can be a chamber 216 capable of holding the individual 104. The individual 104 is a person, such as one suffering from post traumatic stress disorder (PTSD) and having brainwave patterns that may have erratic, non-standard, or otherwise undesirable frequencies. The environment 106 can be filled with a solution, such as saline water, so that the individual 104 floats within. Alternatively, the solution may be a diamagnetic solution. The diamagnetic solution is capable of expressing a magnetic field in opposition to an externally applied electromagnetic field device 103, such as a tensor, thus causing a repulsive effect. The environment 106 can be heated so that the solution is at a desired temperature, such as body temperature, to provide comfort to the individual 104 in the chamber 216.

In the example of FIG. 1, monitor 108 includes devices for collecting signals emanating from the individual 104 by, for example, an electroencephalogram (EEG) electrocardiogram (ECG/EKG), galvanic skin response sensor, heart rate variability monitor, and other known or convenient monitoring device. The monitor 108 can collect brainwaves emanating from the individual 104 and identify a transition from the original frequency to the desired frequency. In another embodiment, monitor 108 can collect infrared emanations from the individual 104 and the environment 106, which can be used to adjust one or more modules of system 200, discussed below.

Figure 2:
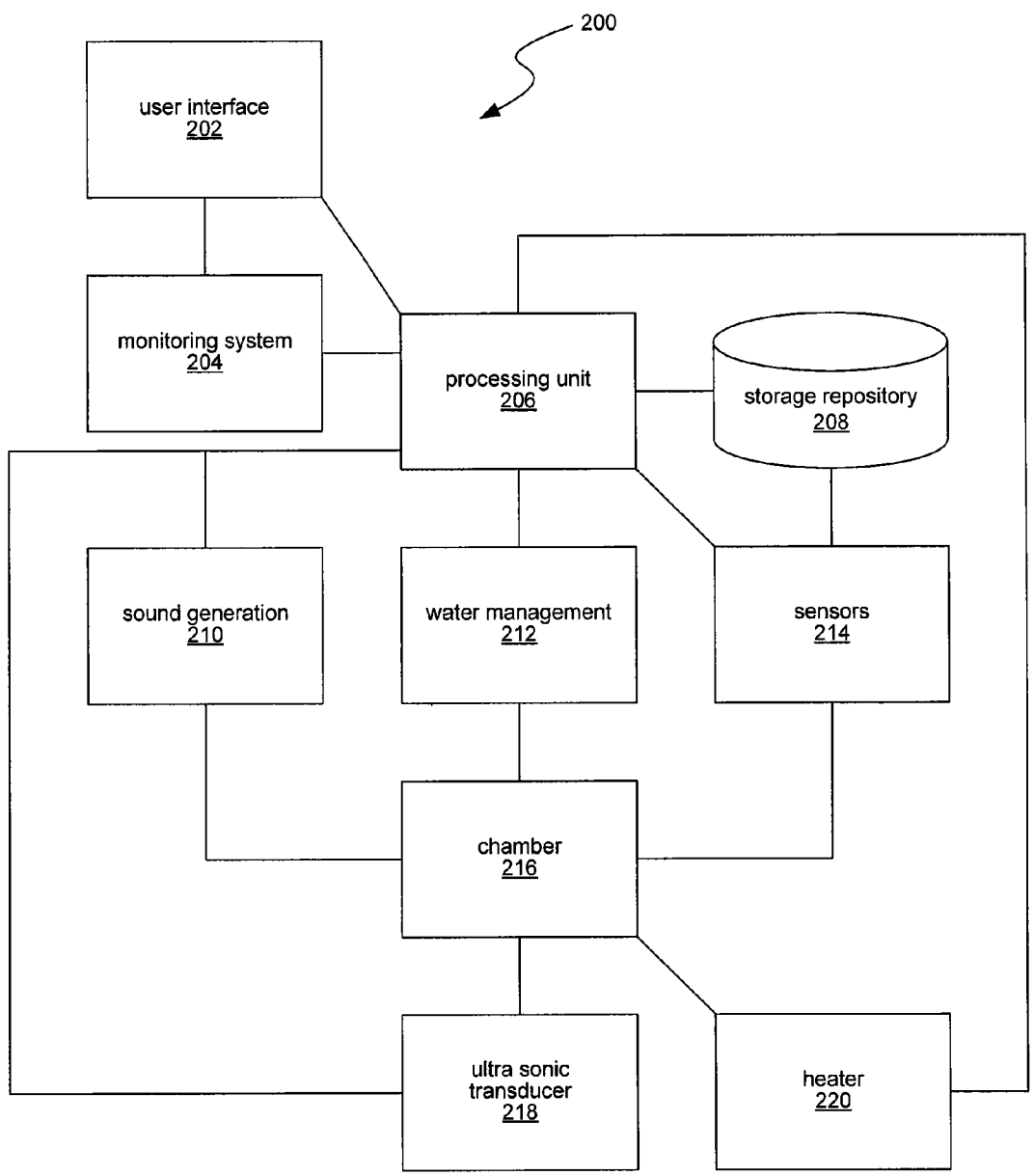
FIG. 2 depicts components of a system for influencing a human brain to operate at a frequency.

FIG. 2. depicts components 202-220 of a system 200 for influencing a human brain to operate at a desired frequency. The components depicted are logically represented as modules of various individual systems; however, one or more components 202-220 may be combined or divided to provide functionality to a particular solution. FIG. 2 includes user interface 202, monitoring system 204, processing unit 206, storage 208, sound generation 210, water management 212, sensors 214, chamber 216, ultra sonic transducer 218, and heater 220.

Figure 2A:
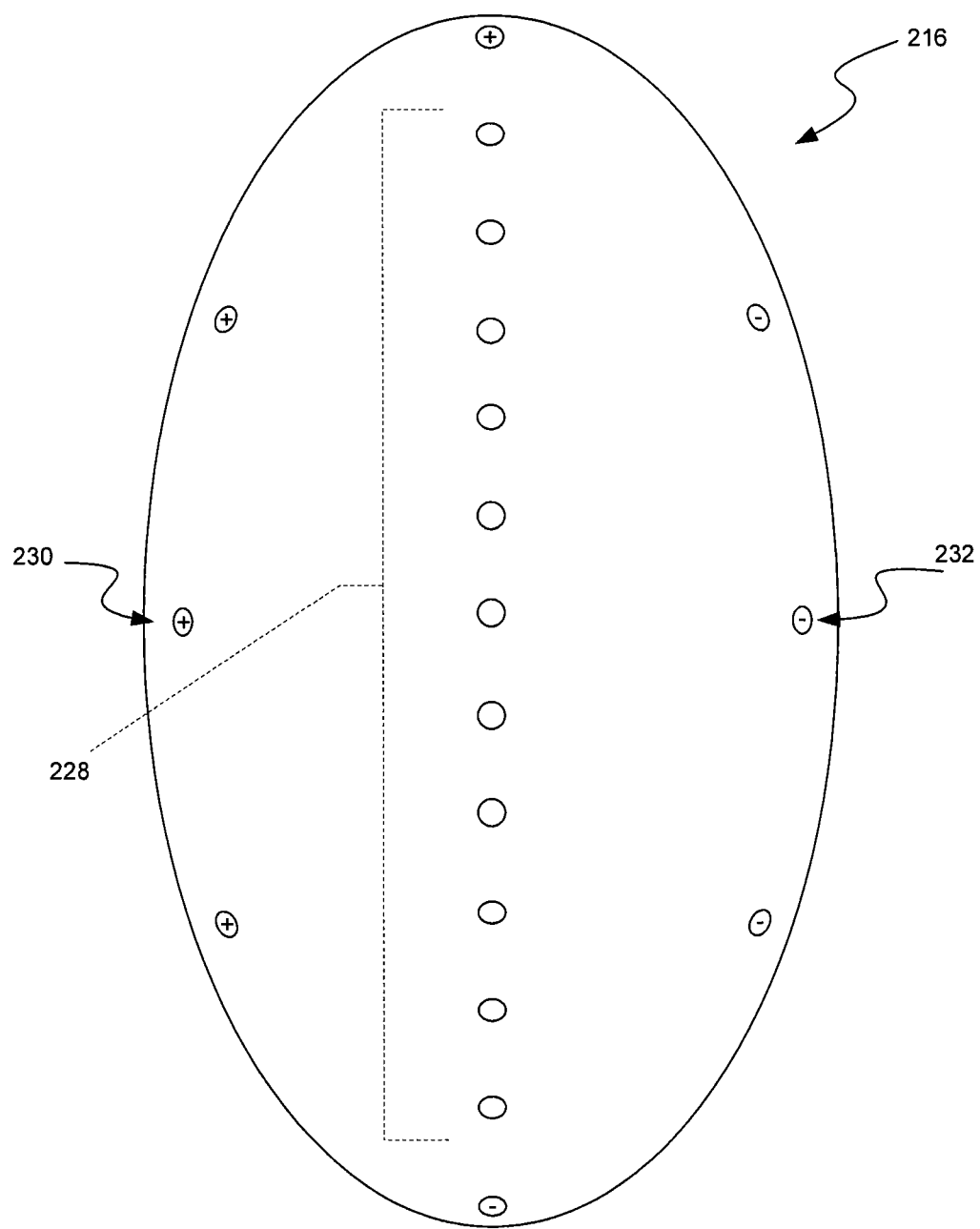
FIG. 2a depicts an example of a chamber used for influencing a human brain to operate at a frequency.

The chamber 216 is illustrated in greater detail in FIG. 2a. Chamber 216 can be constructed so that it is large enough to hold an adult individual 104 while the individual 104 floats in a solution within the chamber 216. In designing the chamber 216, the walls can be spaced so as to provide optimal acoustics for experiencing the sound. In some embodiments, the walls of the chamber 216 are designed based on the acoustical resonance characteristics of a musical instrument. For example, in one embodiment the chamber 216 is based on a cello's design to produce acoustics optimized for delivering beats to the individual 104 within the chamber 216. In another embodiment, the chamber 216 is based on dimensions derived using vaastu architecture. Vaastu shastra is a traditional Hindu system of building design based on directional alignments and mathematical dimensions. Vaastu-based architecture is one technique that can be used by the chamber 216 to transmit a wavelength of light and/or sound to affect cellular regeneration by stimulating cellular fluid. In humans, in response to the stimulation, cells within the brain can respond by entraining to the wavelength transmitted by the chamber 216.

The chamber 216 can be "tuned" based on manipulating its dimensions to generate specific, desirable frequencies used in various therapeutic treatments, such as PTSD, and other applications. In one embodiment, dimensions of the chamber 216 are based on a golden ratio associated with the Fibonacci sequence, or a Fibonacci-like sequence, such as 1:2:3:5:8:5:3:2:1. By definition, the first two Fibonacci numbers are 0 and 1, and each subsequent number is the sum of the previous two. The middle number (e.g. "8" in the example above) of the sequence can represent a center point within the chamber 216. Based on the Fibonacci ratio, concave and convex curves of the outer confines of the chamber 216 can be tuned to produce a desired wavelength of light for generating musical tonal waves.

Parabolic curves or semi-circle structures ("curves") within the chamber 216 can be used to redirect the light back to the center point. In a particular embodiment, a curve at the center point can have golden rectangular dimension of sqrt(5)/2, and successive curves can extend from each direction of the center point to end with a maximum radius at the end of the inner golden rectangle.

Golden rectangle-based dimensions can be used within the center structure of the chamber 216. In one embodiment, the ratio of the width of the golden rectangle to its length is 1:1.618, and the outer body of the chamber 216 has a ratio is 1:1.618. The inner and outer rectangle can have a ratio of 4:5 to create 4:5 relational tuning.

In a particular embodiment, a golden arc ratio of 1:2, 4:5, 2:3 is used to tune the chamber 216 based upon a major 3rd 4:5 ratio. The minimum width can be based on Vaastu architectural parameters. The dimension of the ratio can increase from the center point of chamber 216 to expand out to a 1:1 ratio form center point and then 1:2 ratio on both sides of center line resulting in an example sequence, 5:2:1:1:2:5.

In the example of FIG. 2, one or more ultrasonic transducers 218 can be devices for generating vibrations to stimulate an individual 104 floating in chamber 216. The ultrasonic transducers 218 can be coupled to the processing unit 206 to receive signals to reproduce as ultrasonic waves. In a preferred environment, the ultrasonic vibration is in a range of 0.1-10 HZ to cause micro-adjustments to the ear canal processing the vibration.

As shown in FIG. 2a, a series of transducers 228 can be coupled to chamber 216. In one embodiment, an ultrasonic transducer 218 has a magnetically positive first end 230 and a magnetically negative second end 232. When positioned along opposing sides of the chamber 216, the negative end 232 of one ultrasonic transducer 218 interacts with the positive end 504 of another ultrasonic transducer 230 to produce a magnetic field within the chamber 216. The magnetic field can act as the tensor field to interact, in the chamber 216, with a diamagnetic solution to produce a repulsive effect having a therapeutic effect on the individual 104. In some embodiments, the tensor field can direct the diamagnetic solution in a constant flow around an individual floating in the diamagnetic solution. Alternatively, the chamber 216 may be filled with a saline solution.

In one embodiment, heater 220 may be a far-infrared (FIR) heater. The FIR heater 220 heats ambient air in the chamber 216 at a wavelength to facilitate FIR penetration into bone marrow, for example. The FIR heater 220 can operate at a selectable range of 4-1000 microns to provide high absorption by the human body and deep penetration of the skin.

In the example of FIG. 2, user interface 202 can be a physical interface, a graphical interface, or another known or convenient interface for the monitoring system 204. The user interface 202 can receive instructions from an attendant controlling the stimulation of the individual 104. For example, the user interface 202 can be used to start and stop stimulation, select a type of music to play, control water temperature, display data about the individual, and provide any other known or convenient data about the individual receiving the stimulation.

In the example of FIG. 2, monitoring system 204 can include devices for displaying data to an attendant monitoring stimulation of an individual in the chamber 216. For example, a panel display, CRT (cathode ray tube) display, or other monitoring device may be used. The attendant may be a human person, an operating process within the processing unit 206, or a combination of both.

In the example of FIG. 2, processing unit 206 can be a system or device for analyzing biometric data from sensors. For example, processing unit 206 can be a conventional processor coupled to a memory storing instructions for execution by the processor to use in reducing the electrical signals produced by the sensors to graphs, charts, and other human interpretable representations.

In the example of FIG. 2, storage repository 208 can include data collected from the individual 104. As used in this paper, a repository 208 can be implemented, for example, as software embodied in a physical computer-readable medium on a general- or specific-purpose machine, in firmware, in hardware, in a combination thereof, or in any applicable known or convenient device or system. The repositories described in this paper are intended, if applicable, to include any organization of data, including trees, tables, comma-separated values (CSV) files, traditional databases (e.g., SQL), or other known or convenient organizational formats.

In an example of a system where a repository is implemented as a database, a database management system (DBMS) can be used to manage the repository. In such a case, the DBMS may be thought of as part of the repository or as part of a database server, or as a separate functional unit (not shown). A DBMS is typically implemented as an engine that controls organization, storage, management, and retrieval of data in a database. DBMSs frequently provide the ability to query, backup and replicate, enforce rules, provide security, do computation, perform change and access logging, and automate optimization. Examples of DBMSs include Alpha Five, DataEase, Oracle database, IBM DB2, Adaptive Server Enterprise, FileMaker, Firebird, Ingres, Informix, Mark Logic, Microsoft Access, InterSystems Cache, Microsoft SQL Server, Microsoft Visual FoxPro, MonetDB, MySQL, PostgreSQL, Progress, SQLite, Teradata, CSQL, OpenLink Virtuoso, Daffodil DB, and OpenOffice.org Base, to name several.

Database servers can store databases, as well as the DBMS and related engines. Any of the repositories described in this paper could presumably be implemented as database servers. It should be noted that there are two logical views of data in a database, the logical (external) view and the physical (internal) view. In this paper, the logical view is generally assumed to be data found in a report, while the physical view is the data stored in a physical storage medium and available to a specifically programmed processor. With most DBMS implementations, there is one physical view and an almost unlimited number of logical views for the same data.

In the example of FIG. 2, sound generation unit 210 can include speakers or other devices for reproducing sound to stimulate an individual. In one embodiment, the sound generation unit 210 can operate in a range that resonates with an organ of the individual 104, such as for example, the stomach, spleen, pancreas, lungs, kidneys, liver, heart, large intestines, small intestine, thyroid, or gallbladder. The sound generation unit 210 can be installed using waterproof speakers or transducers embedded in the chamber 216. Alternatively, speakers could be placed above water, mobile for relocation to various positions, and otherwise installed as is known or convenient.

In the example of FIG. 2, sensors 214 can include sensors for collecting biometric data from an individual, such as those sensors discussed in reference to monitor 108.

In the example of FIG. 2, water management unit 212 can include piping, tubing, or other systems for moving water and/or a solution to and from the chamber 216. Additionally, water management unit 212 can include pumps or other devices for moving the water and/or solution to and from the chamber 216 in a continuous re-circulating slow flow.

In the example of FIG. 2, heater 220 can be a device for altering the temperature of the fluid in the chamber 216 to the individual's 104 body temperature, or higher or lower temperatures. Heater 220 may include a sensor to determine the temperature of the fluid in the chamber 216. In one embodiment, Heater 220 utilizes an inline water heater.

Figure 3:
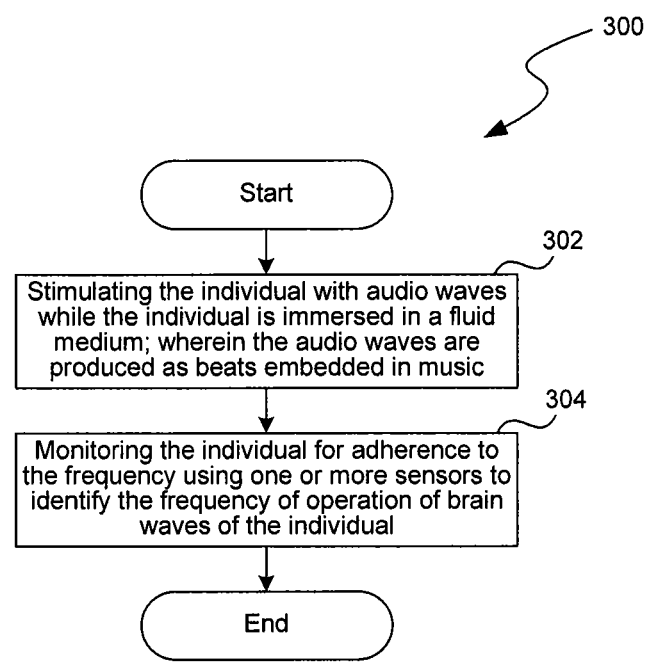
FIG. 3 depicts a flowchart of an example of a method for influencing a human brain to operate at a frequency.

FIG. 3 depicts a flowchart of an example of a method 300 for influencing a human brain to operate at a frequency. The method is organized as a sequence of modules in the flowchart 300. However, it should be understood that these and other modules associated with other methods described herein may be reordered for parallel execution or into different sequences of modules.

In the example of FIG. 3, the flowchart starts at module 302 with stimulating the individual with audio waves while the individual is floating in a fluid medium, wherein the audio waves are produced as beats embedded in music. Cellular regeneration is induced by the audio waves to affect brainwave entrainment. The music can include a track that is interesting, entertaining, soothing or otherwise desirable. The beats can be embedded in this music as a second track mixed in with the music that is audible but may be barely noticeable. In this way, an individual listening to the music can be stimulated by the beat while enjoying the music. In an alternative embodiment, the beats are produced without an accompanying musical track.

In some embodiments, an audio track or audio waves is mixed with a first beat having a first frequency and a second beat having a second frequency, where the chamber 216 has a shape of a rectangle, and where sides of the rectangle have a proportion corresponding to the difference in frequency of the first frequency of the first beat and the second frequency of the second beat. Further, in some embodiments, the audio waves are projected through the aqueous solution in the chamber in a first direction at the first frequency and in a second direction at the second frequency.

One designing the music can take into account the desires of the individual to be stimulated with the beat as well as the kind of stimulation that the individual requires. For example, an individual requiring a relaxing therapeutic session can receive a beat in the theta ($\theta$) range whereas an individual requiring a focused stimulating session can receive a beat in the alpha ($\alpha$) range. Through exposure to the beat, the brain can respond to the beat and after multiple sessions the brain can begin to adopt the beat.

In the example of FIG. 3, the flowchart continues to module 304 which monitors the biofeedback from the individual 104 for adherence to the desired frequency by utilizing one or more sensors that identify the individual's 104 operating brain frequencies. Prior to receiving the stimulation, the individual's 104 brain waves may not operate at the desired frequency. While stimulating the individual with the beat, the brain can adhere to, and begin to operate at, the desired frequency by resonating the beat's slow oscillation frequency with the hippocampus. This can induce and entrain, for example, a relaxed state or a focused state in the brain of the individual. Sensors can collect the brain waves emanating from the individual, and an attendant can monitor the brain waves for adherence to the frequency. Having monitored the individual for adherence to the frequency, the flowchart terminates.

The system 400 may be a conventional computer system that can be used as a client computer system, such as a wireless client or a workstation, or a server computer system. The system 400 includes a device 402, I/O devices 404, and a display device 406. The device 402 includes a processor 408, a communications interface 410, memory 412, display controller 414, non-volatile storage 416, I/O controller 418, clock 422, and radio 424. The device 402 may be coupled to or include the I/O devices 404 and the display device 406.

The device 402 interfaces to external systems through the communications interface 410, which may include a modem or network interface. It will be appreciated that the communications interface 410 can be considered to be part of the system 400 or a part of the device 402. The communications interface 410 can be an analog modem, ISDN modem or terminal adapter, cable modem, token ring IEEE 802.5 interface, Ethernet/IEEE 802.3 interface, wireless 802.11 interface, satellite transmission interface (e.g. "direct PC"), WiMAX/IEEE 802.16 interface, Bluetooth interface, cellular/mobile phone interface, third generation (3G) and fourth generation (4G) mobile phone interfaces, code division multiple access (CDMA) interface, Evolution-Data Optimized (EVDO) interface, general packet radio service (GPRS) interface, Enhanced GPRS (EDGE/EGPRS), High-Speed Downlink Packet Access (HSPDA) interface, or other interfaces for coupling a computer system to other computer systems.

The processor 408 may be, for example, a conventional microprocessor such as an Intel Pentium microprocessor or Motorola power PC microprocessor. The memory 412 is coupled to the processor 408 by a bus 420. The memory 412 can be Dynamic Random Access Memory (DRAM) and can also include Static RAM (SRAM). The bus 420 couples the processor 408 to the memory 412, also to the non-volatile storage 416, to the display controller 414, and to the I/O controller 418.

The I/O devices 404 can include a keyboard, disk drives, printers, a scanner, and other input and output devices, including a mouse or other pointing device. The display controller 414 may control in the conventional manner a display on the display device 406, which can be, for example, a cathode ray tube (CRT) or liquid crystal display (LCD). The display controller 414 and the I/O controller 418 can be implemented with conventional well known technology.

The non-volatile storage 416 is often a magnetic hard disk, flash memory, an optical disk, or another form of storage for large amounts of data. Some of this data is often written, by a direct memory access process, into memory 412 during execution of software in the device 402. One of skill in the art will immediately recognize that the terms "machine-readable medium" or "computer-readable medium" includes any type of storage device that is accessible by the processor 408.

Clock 422 can be any kind of oscillating circuit creating an electrical signal with a precise frequency. In a non-limiting example, clock 422 could be a crystal oscillator using the mechanical resonance of vibrating crystal to generate the electrical signal.

The radio 424 can include any combination of electronic components, for example, transistors, resistors and capacitors. The radio is operable to transmit and/or receive signals.

The system 400 is one example of many possible computer systems which have different architectures. For example, personal computers based on an Intel microprocessor often have multiple buses, one of which can be an I/O bus for the peripherals and one that directly connects the processor 408 and the memory 412 (often referred to as a memory bus). The buses are connected together through bridge components that perform any necessary translation due to differing bus protocols.

Figure 4:
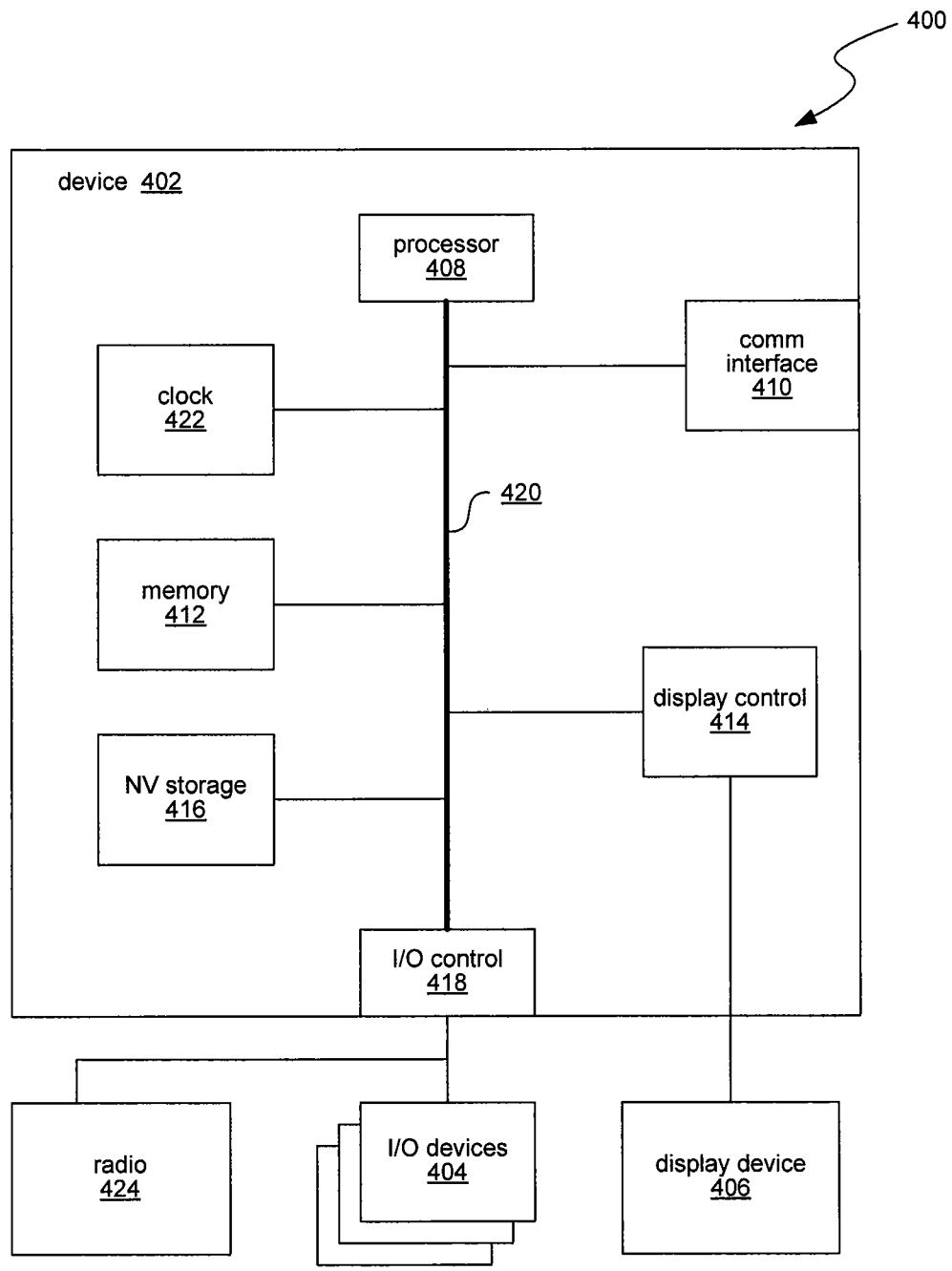
FIG. 4 depicts an example of a computing system representative of the computing systems discussed herein.

Network computers are another type of computer system that can be used in conjunction with the teachings provided herein. Network computers do not usually include a hard disk or other mass storage, and the executable programs are loaded from a network connection into the memory 412 for execution by the processor 408. A Web TV system, which is known in the art, is also considered to be a computer system, but it may lack some of the features shown in FIG. 4, such as certain input or output devices. A typical computer system will usually include at least a processor, memory, and a bus coupling the memory to the processor.

In addition, the system 400 is controlled by operating system software which includes a file management system, such as a disk operating system, which is part of the operating system software. One example of operating system software with its associated file management system software is the family of operating systems known as Windows® from Microsoft Corporation of Redmond, Wash., and their associated file management systems. Another example of operating system software with its associated file management system software is the Linux operating system and its associated file management system. The file management system is typically stored in the non-volatile storage 416 and causes the processor 408 to execute the various acts required by the operating system to input and output data and to store data in memory, including storing files on the non-volatile storage 416.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present example also relates to apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, read-only memories (ROMs), random access memories (RAMs), EPROMs, EEPROMs, flash memory, magnetic or optical cards, any type of disk including floppy disks, optical disks, CD-ROMs, and magnetic-optical disks, or any type of media suitable for storing electronic instructions, and each coupled to a computer system bus.

The algorithms and displays presented herein are not inherently related to any particular computer or other apparatuses. Various general purpose systems may be used with programs in accordance with the teachings herein, or it may prove convenient to construct a more specialized apparatus to perform the required method steps. The required structure for a variety of these systems will appear from the description below. In addition, the present example is not described with reference to any particular programming language, and various examples may thus be implemented using a variety of programming languages.

It will be appreciated to those skilled in the art that the preceding examples are exemplary and not limiting. It is intended that all permutations, enhancements, equivalents, and improvements thereto that are apparent to those skilled in the art upon a reading of the specification and a study of the drawings are included within the true spirit and scope of the present disclosure. It is therefore intended that the following appended claims include all such modifications, permutations and equivalents as fall within the true spirit and scope of these teachings.

What is claimed is:

1. A system comprising:
   a chamber filled with a liquid medium;
   a waterproof speaker, immersed in the liquid medium, configured to generate a plurality of frequencies, wherein at least one frequency is a frequency in a brainwave frequency range adapted to stimulate an individual, floating in the liquid medium, with a monaural beat at a desired frequency within a 4-12 Hz range, wherein a difference between the plurality of frequencies generates the monaural beat at the desired frequency;
   a plurality of sensors for collecting signals from the individual, the signals comprising at least a brainwave at an original frequency; and
   a processing device coupled to the plurality of sensors, the processing device configured to identify the brainwave at the original frequency and monitor the brainwave for transition from the original frequency to the desired frequency.

2. The system of claim 1, further comprising a galvanic skin response sensor and a device selected from a group consisting of a device that generates an electroencephalogram based on brain electrical activity, a device that generates an electrocardiogram based on heart electrical activity, and a heart-rate-variability monitor.

3. The system of claim 2, further comprising a user interface for managing a stimulation of the individual.

4. The system of claim 1, further comprising a repository storing the signals.

5. The system of claim 1, wherein the waterproof speaker comprises one or more speakers to provide audible waves to the individual.

6. The system of claim 1, further comprising a monitoring device coupled to the processing device and a user interface.

7. The system of claim 1, wherein the chamber further comprises an infrared heater for heating the liquid medium inside the chamber.

8. The system of claim 1, wherein the plurality of sensors comprises an infrared camera to monitor the body temperature of the individual.

9. A method of influencing a brain of an individual to operate at a desired frequency comprising:
   stimulating the individual, floating in a liquid medium, with light, a magnetic field, and a plurality of frequencies,
   wherein the plurality of frequencies comprise at least one frequency in a brainwave frequency range, wherein the plurality of frequencies are projected through the liquid medium,
   wherein a difference between the plurality of frequencies generates a monaural beat at the desired frequency within a 4-12 Hz range, and further wherein the monaural beat is generated based on a design of a container, wherein a plurality of ratios associated with the container comprise two of a length associated with walls of the container, a width associated with the walls of the container, and a depth associated with the walls of the container, the plurality of ratios designed to enable the container to resonate at the brainwave frequency range, the brainwave frequency range comprising frequencies within a 4-12 Hz range; and while stimulating the individual, monitoring the individual for adherence to the desired frequency using one or more sensors to identify an original brainwave frequency of the individual's brain.

10. The method of claim 9, wherein part or all of the plurality of frequencies comprise a musical track mixed with a first beat having a first frequency and a second beat having a second frequency.

11. The method of claim 10, wherein part or all of the plurality of frequencies are projected through the liquid medium in a first direction at the first frequency.

12. The method of claim 11, wherein part or all of the plurality of frequencies are projected through the liquid medium in a second direction at the second frequency.

13. The method of claim 10, further comprising heating, via an infrared heater, ambient air surrounding the individual.

14. The method of claim 10, further comprising monitoring, via an infrared camera, the individual's body temperature.

15. The method of claim 9, wherein the liquid medium is a saline solution.

16. The method of claim 9, wherein the liquid medium is a diamagnetic solution.

17. The method of claim 16, further comprising creating an electromagnetic field tensor to cause the diamagnetic solution to direct in a constant flow around the individual.

18. A system comprising:
   a container holding a liquid medium, wherein a plurality of ratios associated with the container comprise two of a length associated with walls of the container, a width associated with the walls of the container, and a depth associated with the walls of the container, the plurality of ratios designed to enable the container to resonate at a brainwave frequency range, the brainwave frequency range comprising frequencies within a 4-12 Hz range;

a waterproof speaker, immersed in the liquid medium, configured to generate a plurality of frequencies, wherein at least one frequency is a frequency in the brainwave frequency range adapted to stimulate an individual, floating in the liquid medium, with a monaural beat at a desired frequency within a 4-12 Hz range, wherein a difference between the plurality of frequencies generates the monaural beat at the desired frequency.

19. The system of claim 18, further comprising a means for stimulating the individual including a far infrared heater.

20. The system of claim 18, wherein the liquid medium is a diamagnetic solution, and wherein the system further comprises a means for creating an electromagnetic tensor field to influence the diamagnetic solution to flow in a direction around the individual.

21. The system of claim 18, further comprising:

a means for collecting signals emanating from the individual, the signals comprising a frequency of brainwaves of the individual; and a means for processing the signals to identify a transition of the brainwaves of the individual from an original frequency to the desired frequency in response to a stimulation.

22. The system of claim 21, wherein the means for collecting signals comprises a far infrared camera and, the signals further comprise the individual's radiated thermal energy.

* * * * *